US006394965B1

(12) United States Patent
Klein

(10) Patent No.: US 6,394,965 B1
(45) Date of Patent: May 28, 2002

(54) TISSUE MARKING USING BIOCOMPATIBLE MICROPARTICLES

(75) Inventor: Dean A. Klein, North Oaks, MN (US)

(73) Assignee: Carbon Medical Technologies, Inc., St. Paul, MN (US)

( * ) Notice: Subject to any disclaimer, the term of this patent is extended or adjusted under 35 U.S.C. 154(b) by 22 days.

(21) Appl. No.: 09/638,964

(22) Filed: Aug. 15, 2000

(51) Int. Cl.⁷ .............................................. A61B 10/00
(52) U.S. Cl. ...................................... 600/564; 600/431
(58) Field of Search .................................. 606/186, 116, 606/117; 600/421

(56) References Cited

U.S. PATENT DOCUMENTS

| | | |
|---|---|---|
| 3,334,050 A | 8/1967 | Grotenhuis et al. |
| 3,746,650 A | 7/1973 | Lahr et al. |
| 4,341,220 A | 7/1982 | Perry |
| 4,627,853 A | 12/1986 | Campbell et al. |
| 4,709,703 A | 12/1987 | Lazarow et al. |
| 4,795,463 A | 1/1989 | Gerow |
| 4,997,454 A | 3/1991 | Violante et al. |
| 4,999,188 A | 3/1991 | Solodovnik et al. |
| 5,108,399 A | 4/1992 | Eitenmuller et al. |
| 5,202,352 A | 4/1993 | Okada et al. |
| 5,236,410 A | 8/1993 | Granov et al. |
| 5,366,507 A | 11/1994 | Scottosanti |
| 5,382,260 A | 1/1995 | Dormandy, Jr. et al. |
| 5,441,517 A | 8/1995 | Kensey et al. |
| 5,451,406 A | 9/1995 | Lawin et al. |
| 5,476,472 A | 12/1995 | Dormandy, Jr et al. |
| 5,624,685 A | 4/1997 | Takahashi et al. |
| 5,635,215 A | 6/1997 | Boschetti et al. |
| 5,648,100 A | 7/1997 | Boschetti et al. |
| 5,665,092 A | 9/1997 | Mangiardi et al. |
| 5,676,146 A | 10/1997 | Scarborough |
| 5,702,361 A | 12/1997 | Evans et al. |
| 5,746,734 A | 5/1998 | Dormandy, Jr. et al. |
| 5,792,478 A | 8/1998 | Lawin et al. |
| 5,830,230 A | 11/1998 | Berryman et al. |
| 5,891,058 A | 4/1999 | Taki et al. |
| 5,894,022 A | 4/1999 | Ji et al. |
| 5,902,310 A | 5/1999 | Foerster et al. |
| 5,941,890 A | 8/1999 | Voegele et al. |
| RE36,461 E | 12/1999 | Russell et al. |
| 6,015,424 A | 1/2000 | Rosenbluth et al. |
| 6,017,977 A | 1/2000 | Evans et al. |
| 6,056,700 A | 5/2000 | Burney et al. |
| 6,083,202 A * | 7/2000 | Smith ........................ 604/164 |
| 6,086,544 A | 7/2000 | Hibner et al. |
| 6,161,034 A | 12/2000 | Burbank et al. |

FOREIGN PATENT DOCUMENTS

| | | |
|---|---|---|
| WO | WO 94/21196 | 9/1994 |
| WO | WO 96/08208 A1 | 3/1996 |
| WO | WO 99/12577 | 3/1999 |
| WO | WO 99/43366 | 9/1999 |
| WO | WO 99/43380 | 9/1999 |
| WO | WO 99/44643 | 9/1999 |
| WO | WO 00/38579 | 7/2000 |
| WO | WO 01/00101 | 1/2001 |

OTHER PUBLICATIONS

Beavan, Al., "Material Properties and Applications of Pyrolite® Carbon", as published in Materials Engineering, Feb. 1990, pp. 1–5.

Malizia, Anthony A., Jr., Reiman, Herbert M., Meyers, Robert P., Sande, Jonathan R., Barham, Steven S., Benson, Ralph C., Jr., Dewanjee, Mrinal K., and Utz, William J., "Migration and Granulomatous Reaction After Periurethral Injection of Polytef (Teflon)," JAMA, Jun. 22/29, 1984 vol. 251, No. 24.

Goldberg, Ronald P., MD, Hall, Ferris M., M.D., and Simon, Morris, MD. "Preoperative Localization of Non–Palpable Breast Lesions Using a Wire Marker and Perforated Mammographic Grid," Radiology 146:833–835, Mar. 1983.

Fajardo, Laurie L., MD, Bird, Richard E., MD, Herman, Cheryl R., MD, DeAngalis, Gia A., MD, "Placement of Endovascular Embolization Microcoils to Localize the Site of Breast Lesions Removal at Sterotactic Core Biopsy," Radiology, 1998, 206:275–278.

Liberman, Laura, MD, Dershaw, David, MD, Morris, Elizabeth A., MD, Abramson, Andrea F., MD, Thorton, Cynthia M., RT (R)(M), Rosen Paul Peter, MD, "Clip Placement After Stereotactic Vacuum–Assisted Breast Biopsy," Radiology, 1997; 205:417–422.

Burbank, Fred, MD, Farcier, Nancy, MD, "Tissue Marking Clip for Stereotactic Breast Biopsy: Initial Placement Accuracy, Long–term Stability, and Usefulness as a Guide for Wire Localization," Radiology 1997;205:407–415.

Jonathan I., Epstein MD, "Are You Getting The Maximum Diagnostic and Prognostic Information from your Prostate Needle Biopsy?" Contemporary Urology, Apr. 1999, pp. 106–118.

Berman, MF., Hartmann A., Mast H., Sciacca RR., Mohr JP., Pile–Spellman J., Young WL., "Determinants of Resource Utilization in the Treatment of Brain Arteriovenous Malformations," Ajnr: American Journal of Neuroradiology, 20(10):2004–8, 1999 Nov.–Dec.

Abel, G., and Czop, J.K., "Stimulation of Human Monocyte B–glucan Receptors by Glucan Particles Induces Production of TNF–∂ and 1L–B," *Int. J. Immunopharmacol.*, 14(8):1363–1373, 1992.

(List continued on next page.)

Primary Examiner—Samuel G. Gilbert
Assistant Examiner—Pamela Wingood
(74) Attorney, Agent, or Firm—Faegre & Benson LLP

(57) ABSTRACT

Described are methods of tissue marking using microparticles that have carbon surfaces, and that contain a contrast agent. Preferred microparticles include a permanently radiopaque particle substrate and a pyrolytic carbon surface.

2 Claims, No Drawings

OTHER PUBLICATIONS

Nagino M., Kamiya J., Kanai M., Uesaka K., Sano T., Yamamoto H., Hayakawa N., Nimura Y., "Right Trisegment Portal Vein Embolization for Biliary Tract Carcinoma: Technique and Clinical Utility," Surgery, 127(2):155–60, 2000 Feb.

(Abstract) Kalman D., Varenhorst E., "The Role of Arterial Embolization in Renal Cell Carcinoma," Scandinavian Journal of Urology & Nephrology, 33(3):162–70, 1999 Jun.

(Abstract) Lee W., Kim TS., Chung JW., Han JK., Kim SH., Park JH., "Renal Angiomyolipoma: Embolotherapy with a Mixture of Alcohol and Iodized Oil," Journal of Vascular & Interventional Radiology, 9(2):255–61, 1998 Mar.–Apr.

(Abstract) Layelle I., Flandroy P., Trotteur G., Dondelinger RF., "Arterial Embolization of Bone Metastases: is it Worthwhile?" Journal Belge de Radiologie, 81(5):223–5, 1998 Oct.

(Abstract) Mourikis D., Chatziioannou A., Antoniou A., Kehgias D., Gikas D., Vlahos L., "Selective Arterial Embolization in the Management of Symptomatic Renal Angiomyolipomas", European Journal of Radioloby, 32(3):153–9, 1999 Dec.

Malizia, Jr. MD, Anthony A.; Reiman, MD, Herbert M.; Myers, MD, Robert P.; Sande, Jonathan R.; Barham, PhD, Steven S.; Benson, Jr. MD, Ralph C.; Dewanjee, PhD, Mrinal K.; Utz, William J., Migration and Granulomatous Reaction After Periurethral Injection of Polytef (Teflon), JAMA, Jun. 22/29, 1984: vol. 251, No. 24, pp. 3277–81.

Bruninx, Guy: Wery, Didier; Dubois, Eric; Nakadi, Badih; Van Dueren, Eric; Verhelst, Guy, Delcour, Christian; "Emergency Endovascular Treatment of An Acute Traumatic Rupture of the Thoracic Aorta Complicated by a Distal Low–Flow Syndrome," Cardiovascular & Interventional Radiology, 22(6):515–518, 1999 Nov.–Dec.

Mitsuzaki K., Yamashita Y., Utsunomiva D., Sumi S., Ogata I., Takahashi M., Kawakami S., Ueda S., "Balloon–Occluded Retrograde Transvenous Embolization of a Pelvic Arteriovenous Malformation," Cardiovascular & Interventional Radiology 22(6):518–20, 1999 Nov.–Dec.

Dutta, Usha; Garg, Pramod K.; Agarwal, Rajeev; Gupta, S. Dutta; Prasad, G.A.; Kaul, Upendra; Tandon, Rakesh K., "Blocking of the Hepatic Vein Outflow by Neointima Covering a Wallstent Across a Membranous Stenosis of the Inferior Vena Cava", Cardiovascular & Interventional Radiology 22(6):521–523, 1999 Nov.–Dec.

Kishimoto, Keiko; Hara, Akihiko; Arita, Takeshi; Tsukamoto, Katsuhiko; Matsui, Norichika; Kaneyuke, Toshihiro; Matsunaga, Naofumi, "Stomal Varices: Treatment by Percutaneous Transhepatic Coil Embolization", Cardiovascular & Interventional Radiology 22(6):523–525, 1999 Nov.–Dec.

Shi HB., Suh DC., Lee HK., Lim SM., Kim DH., Choi CG., Lee CS., Rhim SC., "Preoperative Transarterial Embolization of Spinal Tumor: Embolization Techniques and Results," Ajnr: American Journal of Neuroradiology, 20(10):2009–15, 1999 Nov.–Dec.

* cited by examiner

TISSUE MARKING USING BIOCOMPATIBLE MICROPARTICLES

BACKGROUND

Tissue marking generally is a method of marking a position in a body, such as a specific position on tissue or an organ, to allow re-visiting of the position at a later time to check for progress or developments of an ailment or a treatment, or to allow re-treatment at the same site. As an example, tissue marking can be used during biopsy or other tissue-removal procedures to accurately mark the site of the tissue-removal or biopsy, to allow a treatment-giver to later return to the same site if desired, e.g., to monitor the status of the tissue in question, or to do another biopsy.

Such tissue marking can be useful in procedures relating to colon or rectum biopsies or tissue removal, prostrate biopsies, or breast biopsies.

Specifically with respect to breast biopsies, it is not uncommon in modern breast biopsies, e.g., using a mammotone breast biopsy system sold under the trademark name BIOPSYS, from Ethicon Endo-Surgery, Inc., for all evidence of a lesion to be removed during biopsy. Removing all trace of the tissue also removes identifying features from the site, and makes it difficult to return to the same location later, to re-check the site. This dilemma, created by a removal of a potentially malignant breast mass or cluster of microcalcifications during core biopsy, can be ameliorated by placing radiographically visible markers immediately after the biopsy. The marker, e.g., a radiopaque material, can be used to help locate the biopsy site in case malignancy is determined, thereby enabling return to the same site and optionally a subsequent treatment such as surgical excision, even if the mammographic findings associated with the original lesions were removed completely.

One localization method involves placing a metallic clip (e.g., sold under the trade name Micromark™, from Biopsys Medical) through an 11- or 14-gauge probe of a motorized, vacuum core-cutting biopsy device, and attaching the clip to the site of a biopsy, to mark the location of the biopsy. Such clips measure approximately 3 mm across, and are permanent and radiopaque. The use of marking clips has been described in the following articles: Burbank, Fred, MD, Farcier, Nancy, MD, "Tissue Marking Clip for Stereotactic Breast Biopsy: Initial Placement Accuracy, Long-term Stability, and Usefulness as a Guide for Wire Localization," Radiology 1997; 205:407–415; Liberman, Laura, MD, Dershaw, David, MD, Morris, Elizabeth A., MD, Abramson, Andrea F., MD, Thorton, Cynthia M., R T (R)(M), Rosen Paul Peter, MD, "Clip Placement After Stereotactic Vacuum-Assisted Breast Biopsy," Radiology, 1997; 205:417–422.

Another example of an application for tissue marking is in prostate biopsies. It is recognized that initial biopsies may not be fully determinative in the prostate. See, e.g., Jonathan I., MD, "Are You Getting Maximum Diagnostic and Prognostic Information from your Prostate Needle Biopsy?" Contemporary Urology, 106, April 1999. Tissue marking can ensure that the tissue of non-determinative initial biopsies can be monitored for progressive disease, and that if necessary a follow-up biopsy can be performed at the site of the initial biopsy.

Other methods of tissue marking or "localization" are described in articles of the technical literature: see e.g., Fajardo, Laurie L., MD, Bird, Richard E., MD, Herman, Cheryl R., MD, DeAngalis, Gia A., MD, "Placement of Endovascular Embolization Microcoils to Localize the Site of Breast Lesions Removal at Sterotactic Core Biopsy," Radiology, 1998, 206: 275–278. Still another method of localizing breast lesions is described at Goldberg, Ronald P., MD, Hall, Ferris M., M.D., and Simon, Morris, MD. "Preoperative Localization of Non-Palpable Breast Lesions Using a Wire Marker and Perforated Mammographic Grid," Radiology 146: 833–835, March 1983; see also U.S. Pat. Nos. 4,341,220 and 5,665,092.

SUMMARY OF THE INVENTION

The invention provides a method of tissue marking. The method includes the use of detectable, preferably radiopaque particles delivered to a tissue site for later detection. The particles can preferably be delivered into the body to a desired site by injection using a hypodermic needle and syringe, or another similar instrument, or percutaneously, with the assistance of a biopsy probe. Microparticles can preferably be of an average size in the range from about 100 to 1000 microns, more preferably from about 200 to 500 microns, and most preferably from about 251 to about 300 microns, in transverse, cross-sectional dimension. The microparticles can preferably be permanently radiopaque, and may optionally comprise a carbon coating.

An optional carbon surface may include, for example, pyrolytic carbon, e.g., isotropic carbon such as low temperature isotropic carbon, vitreous carbon, or any other useful form of carbon. The carbon can be coated onto a particle substrate as a thin coating or film, thereby creating a particle having a highly biocompatible carbon surface. While not required, pyrolytic carbon can be preferred.

The particle substrate can be but is not necessarily biocompatible, and should be capable of withstanding the conditions of the process for coating a carbon surface onto the substrate, which might include elevated temperatures. In particularly preferred embodiments, particle substrates can be radiopaque, most preferably permanently radiopaque. Exemplary radiopaque materials can include metals and metal oxides such as zirconium oxide and aluminum oxide, gold, titanium, silver, stainless steel, oxides and alloys thereof, etc.

The microparticles can be delivered using a fluid carrier, which can be any biologically compatible material capable of delivering the microparticles to a desired tissue site, such as a biologically compatible suspension, solution, or other form of a fluid or gel. Examples of materials useful in biologically compatible carriers include saline, dextrans, glycerol, polyethylene glycol, corn oil or safflower, other polysaccharides or biocompatible polymers, methyl cellulose, glucan, agarose, etc., either singly or in combination.

The use of microparticles in tissue marking methods, preferably by injecting through a hypodermic needle and syringe or a like instrument, has advantages over other tissue marking methods. For instance, delivery of microparticles using a needle and syringe allows very precise delivery of microparticle markers to a desired tissue site, this is particularly true if a biopsy probe used to perform a biopsy is used to assist delivery of microparticles for tissue marking, without first moving the biopsy sheath. Additionally, microparticles can be used in tissue locations where other types of tissue markers are not or cannot be used. For example, some tissue locations such as the colon or rectum do not lend themselves to the use of marking clips, yet it is possible to deliver microparticles to these locations for effective marking. And, embodiments of useful microparticles having a carbon-coated surface are very biocompatible. As another advantage, preferred embodiments of the microparticles can be permanently radiopaque, e.g., by virtue of a permanently radiopaque particle substrate. The location of permanently radiopaque particles can be monitored, by known methods, for as long as the radiopaque microparticles remain in a body.

An aspect of the invention relates to a method for tissue marking. The method includes delivering detectable microparticles to a tissue site and detecting the microparticles.

Another aspect of the invention relates to a method of tissue marking. The method includes injecting detectable microparticles to a tissue site through a hypodermic needle, and detecting the microparticles.

Yet another aspect of the invention relates to a method for marking a biopsy. The method includes performing a biopsy and marking the site of the biopsy using detectable microparticles injected through a hypodermic needle.

Yet another aspect of the invention relates to a method for marking a site of tissue removal. The method includes performing a tissue removal procedure and marking the site of the tissue removal using detectable microparticles injected through a hypodermic needle.

For purposes of the present disclosure, the following terms shall be given the following meanings.

The term "biocompatible," refers to materials which, in the amount employed, are non-toxic and substantially non-immunogenic when used internally in a patient, and which are substantially insoluble in blood. Suitable biocompatible materials include ceramics, metals and metal oxides such as titanium, gold, silver, stainless steel, oxides thereof, aluminum oxide, zirconium oxide, etc., carbon such as pyrolytic carbon or low temperature or ultra low temperature isotropic carbon.

The term "detectable" refers to materials capable of being detected during or after injection into a mammalian subject, by methods generally used for monitoring and detecting such materials, e.g. magnetic resonance, X-ray, ultrasound, magnetotomography, electrical impedance imaging, light imaging (e.g. confocal microscopy and fluorescence imaging) and nuclear imaging (e.g. scintigraphy, SPECT and PET). Examples include contrast-enhancing agents such as radiopaque materials. Contrast-enhancing agents may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

DETAILED DESCRIPTION

The invention provides methods of marking tissue for any reason, such as to mark the site of the removal of a tissue, e.g., the removal of a polyp from a colon or rectum; to mark the site of a biopsy, including a breast biopsy, a prostate biopsy, a colon biopsy, a rectum biopsy; or to mark the site of any other medical procedure or removal of tissue or biopsy at another tissue location. The tissue may be marked for any reason, for example to return to the same tissue site to monitor the progress of a medical condition or a treatment, or to perform a subsequent biopsy at the same site. Or, the tissue may be marked to provide a target for radiation treatment, i.e., detectable microparticles can be delivered to a tissue site to act as a target at which or near a beam of radiation can be precisely directed.

The invention, generally stated, involves marking a tissue site using detectable microparticles, preferably that are also biocompatible. The microparticles contain some detectable component (some well-known detectable components are referred to as a "contrast-enhancing agent") that causes the microparticles to be detectable, e.g., allows the microparticles to be tracked, monitored, or otherwise detected by known methods, including radiography or fluoroscopy. The detectable component, e.g., contrast-enhancing agent, can be any material capable of enhancing contrast in a desired imaging modality (e.g. magnetic resonance, X-ray, ultrasound, magnetotomography, electrical impedance imaging, light imaging (e.g. confocal microscopy and fluorescence imaging) and nuclear imaging (e.g. scintigraphy, SPECT and PET)). Contrast-enhancing agents are well known in the medical arts, with any of a variety of such contrast-enhancing agents being suitable for use according to the methods of the invention.

A detectable component is preferably capable of being substantially immobilized within a microparticle, and may be incorporated into a microparticle for use in tissue marking in any of a variety of ways, e.g., as part of a particle substrate, as a surface coating or an additive to a surface coating such as a carbon coating, or elsewhere. In one sense, a detectable component can be added to a material that is not detectable, e.g., not radiopaque. The detectable component may be provided in any location or portion of a microparticle, by known methods. Preferred detectable materials, and their compositions with respect to microparticles, are described below.

According to a preferred mode of the invention, the microparticles comprise a permanently radiopaque material which can be permanently detected within a body following delivery to a tissue site. Permanent radiopacity is unlike contrast-enhancing agents or radiopaque materials which biodegrade or otherwise lose their effectiveness (detectability, e.g., radiopacity) over a period of time, e.g., days or weeks, such as 7 to 14 days. (See, e.g., PCT/GB98/02621). An advantage of permanent radiopaque materials is that they can be detected for as long as they remain in a body, whereas non-permanent radiopaque materials or other types of contrast-enhancing agents are detectable for only a limited time. See generally, Assignee's copending U.S. patent application Ser. No. 09/602,323, entitled Embolization Using Carbon Coated Microparticles, and filed on Jun. 23, 2000, the full disclosure of which is incorporated herein by reference.

Some examples of radiopaque materials include paramagnetic materials (e.g. persistent free radicals) and compounds, salts, and complexes of paramagnetic metal species (for example transition metal or lanthanide ions); heavy atom (i.e. atomic number of 37 or more) compounds, salts, or complexes (e.g. heavy metal compounds, iodinated compounds, etc.); radionuclide-containing compounds, salts, or complexes (e.g. salts, compounds or complexes of radioactive metal isotopes or radiodinated organic compounds); and superparamagentic materials (e.g. metal oxide or mixed oxide particles, particularly iron oxides). Preferred paramagnetic metals include Gd (III), Dy (III), Fe (II), Fe (III), Mn (III) and Ho (III), and paramagnetic Ni, Co and Eu species. Preferred heavy metals include Pb, Ba, Ag, Au, W, Cu, Bi and lanthanides such as Gd, etc.

The amount of detectable material included in a microparticle used for tissue marking should be sufficient to allow detection of the microparticle as desired. The amount used in any particular application or microparticle may depend on various factors such as the size of the microparticles, the total amount of microparticles delivered, the type of contrast-enhancing agent, etc. According to some embodiments of the invention, microparticles can be made up of 100 percent radiopaque material. Alternatively, for radiopaque particles that are coated with a carbon surface, e.g., as described below, the microparticles can have any relative amounts of radiopaque particle substrate to carbon coating that will allow the microparticles to be used as detectable tissue markers, for example from about 50 to 100 percent by weight radiopaque particle substrate based on the total weight of the particle substrate and the carbon coating. Optionally, some, i.e., only a portion, but not all microparticles used in a particular tissue marking procedure (tissue marking composition, as described below) can include a detectable component.

In one preferred embodiment of the invention, the microparticles are completely made up of permanently radiopaque material, preferably in a form that is biologically compatible, and are delivered directly to a tissue site as such.

In another embodiment, microparticles for tissue marking according to the invention can have a surface that comprises carbon. The carbon-containing particle surface may be in the form of a carbon-containing coating or carbon-containing film of any type of carbon, e.g., pyrolytic carbon (such as low temperature isotropic or LTI carbon), another type of isotropic carbon, or vitreous carbon, preferably in a form that is biocompatible. Various forms of carbon are described in the article "Material Properties and Applications of Pyrolite® Carbon," by Al Beavan, as published in *Materials Engineering,* February 1990, incorporated herein by reference. Examples of carbon coated particles are described, e.g., in U.S. Pat. No. 5,792,478, the full disclosure of which is incorporated herein by reference.

The atomic structure of both pyrolytic, e.g., LTI carbon, and vitreous carbon is similar to graphite, a common form of carbon, but the alignment between hexagonal planes of atoms is not as well ordered as in graphite. Pyrolytic carbon is characterized by a more chaotic atomic structure with warped hexagonal planes, missing atoms, and generally a more turbostatic appearance. This results in better bonding between layer planes. See Beavan.

The carbon-coated microparticles can preferably be constructed as a particle substrate having a carbon surface, e.g., a particle substrate having a layer of carbon coated thereon. While the substrate need not be biocompatible due to its being coated with a preferably biocompatible layer comprising carbon, it can be preferred that the particle substrate also be biocompatible.

Such carbon-coated microparticles may be prepared using any of a variety of coating processes to deposit carbon onto a particle substrate. A particle substrate can be selected for compatibility with the coating process, meaning that it should be capable of withstanding temperatures used in a given process for coating carbon onto a particle substrate. Relatively hard metallic or ceramic materials capable of withstanding high temperature conditions of a coating process can generally be preferred materials for a particle substrate. Metals, metal oxides, and alloys, including but not limited to medical grade stainless steel, silver, gold, titanium and titanium alloys, and oxide derivatives of stainless steel or titanium or titanium alloys, are also acceptable materials for the particle substrate, with aluminum oxide, and zirconium oxide being especially suitable. Carbon itself in any of its various forms, e.g., pyrolytic carbon, non-pyrolytic carbon, isotropic carbon, graphite, or vitreous carbon, may be useful as a particle substrate material. Thus, the microparticles may include a carbon coating deposited on a carbon particle substrate, and may be substantially or entirely made of carbon. In one embodiment of the invention, both the particle substrate and the carbon coating may comprise pyrolytic carbon.

Particle substrates intended to be coated with carbon, whatever their composition, should be of sufficient diameter, shape, and uniformity that they can be coated with carbon, as described, to produce carbon-coated particles of a size, quality, and nature as described herein. Preferably, the particle substrates, prior to coating, can be selected and processed, e.g., milled, extruded, sifted, cleaned, filtered, or otherwise formed, etc., to provide a desired combination of particle size, shape, and quality, to result in coated particles of a desired size, shape, and quality.

Pyrolytic carbon can be produced and coated onto a substrate surface by known methods, e.g., as described in the Beavan article, and in U.S. Pat. No. 5,792,478, cited above. Generally, hydrocarbons and alloying gases are decomposed to prepare a pyrolytic carbon coating on a particle substrate. The particle substrates are included with the hydrocarbons and alloying gases in a fluidized or floating bed at a temperature sufficient to cause deposition of pyrolyzed carbon onto the substrate surface, e.g., from about 1200 to 1500 C (see Beavan, p.2). Inert gas flow is used to float the bed of particle substrates, optionally including an inert mixing media. The hydrocarbon pyrolysis results in a high carbon, low hydrogen content carbon material being deposited as a solid material onto the particle substrates.

Alternatively, a carbon coating (sometimes referred to as "ultra-low-temperature isotropic carbon") may be applied to a particle substrate using any one of other various coating processes for depositing carbon, e.g., a vacuum vapor deposition process. Such a method uses ion beams generated from any of a variety of known processes, such as the disassociation of $CO_2$, reactive dissociation in vacuum of a hydrocarbon as a result of a glow discharge, sublimation of a solid graphite source, or cathode sputtering of a graphite source. Gold has been found to be an especially suitable substrate material for vacuum vapor deposited carbon. Other substrates, including but not limited to nickel, silver, stainless steel, or titanium are also quite acceptable as a substrate material for this type of coating process.

The high strength, resistance to breakdown or corrosion, and durability of a carbon surface ensures effective, long term functioning of microparticles in tissue marking applications. The established biocompatibility of carbons such as pyrolytic and vitreous carbon makes the described particles particularly suitable for tissue marking applications. The microparticle substrates may be completely encased by a carbon surface. This results in a smooth coated particle with no substrate exposure on the surface of the particle. Preferred carbon coatings can be in the range of fractions of thousandths of an inch, e.g., about one half of a thousands of an inch (0.0005 inches), on average, covering the surface of the particle substrate.

The microparticles, whether coated or uncoated, are preferably generally rounded particles that have a smooth surface. The smooth surface enhances passage of the microparticles through a hypodermic needle. Microparticles are preferably subjected to a cleaning and sieving process to remove contaminants and to separate out particles of a size less than or greater than a desired size range. The particles may preferably range in size from 100 microns to 1,000 microns in average, transverse cross-sectional dimension, preferably in the range from about 200 to 500 microns, and a particularly preferred size range for use in tissue marking applications can be between about 251 and about 300 microns. To achieve this most preferred such size range, microparticles may be processed, e.g., segregated to a selected size range, for example using a sieving process such that the minimum microparticle dimension will pass through a U.S. No. 50 Screen Mesh (300 micron grid size opening) but will not pass through a U.S. No. 60 Screen Mesh (250 micron grid size). That minimum dimension will be the transverse, cross-sectional dimension on oblong or elongated particles, with that dimension coinciding with the particle diameter on generally spherical particles.

Microparticles can be delivered to a tissue site using any instrument or apparatus that can be used to inject an amount of microparticles, preferably contained or suspended in a carrier, through the skin, mucosa, or through an incision in the skin, to a desired tissue site. Preferred instruments include instruments such as hypodermic needles or other similar needle-like apparatuses, such as any small bore instrument, cannula, etc. (All of these types of instruments will be referred to collectively herein, for convenience, using the term "hypodermic needle" or "needle.") The particular instrument used for delivery is not critical, provided that its components are compatible with the tissue marking composition (described below) (i.e., the apparatus components will not readily degrade in the tissue marking composition, and vice versa).

According to one specific example of a method of delivering microparticles for tissue marking, microparticles can be delivered using a hypodermic needle and a syringe, by inserting the hypodermic needle into a desired tissue site, followed by delivery of the microparticles to the tissue site.

Optionally, any of a variety of surgical or non-invasive or minimally-invasive surgical instruments can also be used to assist in delivery. For example, following removal of a polyp from a colon or a rectum, by known surgical methods, a hypodermic needle can be inserted through the mucosa, at the site of the polyp, to deliver microparticles. As another example, relating to breast biopsies, a mammotone inserted through a small incision in the skin can be maintained in the operative position, and a needle can be inserted through its sheath, to precisely deliver microparticles to the site of biopsy.

Once a needle is in place (e.g., during or soon after a biopsy or tissue removal has been performed) microparticles can be slowly injected through the needle to the desired tissue site. The microparticles are of a size that can be effectively deposited through a hypodermic needle or like instrument, and that will substantially remain at the tissue site where delivered. If the particles are too small, they can be engulfed by the body's white cells (phagocytes) and carried to distant organs or be carried away in the microvasculature and travel until they reach a site of sufficient constriction to prevent further movement. On the other hand, particles should not be so large that they cannot be effectively delivered using a hypodermic needle or the like. For the method of the present invention, a particularly preferred, average microparticle size can be from about 100 to 1000 microns, e.g., 200 to 500 microns, preferably from about 251 to 300 microns, because such sizes can allow injection through small bore instruments and are large enough to avoid migration of the microparticles from the injection site. See generally, Malizia, Anthony A., Jr., Reiman, Herbert M., Meyers, Robert P., Sande, Jonathan R., Barham, Steven S., Benson, Ralph C., Jr., Dewanjee, Mrinal K., and Utz, William J., "Migration and Granulomatous Reaction After Periurethral Injection of Polytef (Teflon)," JAMA, Jun. 22/29, 1984 volume 251, No. 24.

The use of microparticles in tissue marking methods, preferably injected by use of a needle and syringe or a like instrument, has advantages over the use of other tissue marking methods. For instance, delivery of microparticles using a needle and syringe allows very precise delivery of microparticles to a desired tissue site. This is particularly true if the biopsy probe used to perform a biopsy is immediately subsequently used to delivery the microparticles, without first moving the probe sheath. Other advantages are that microparticles can be used where other types of tissue markers either cannot be used, or are not used. Specifically, tissue-marking clips are not used in the colon or rectum, whereas microparticles can be injected to these tissues. Additionally, tissue marking clips can sometimes be inadvertently attached to tissue that will move and cause movement of the clip, such as a ligament. The injection of microparticles avoids such problems.

The amount of microparticles introduced in a tissue marking procedure can be any amount sufficient to mark a location to be detected at a later time. The amount delivered can vary depending on factors such as the size of the microparticles, the amount of detectable component in the microparticles, factors relating to the patient, etc. Such factors will be within the skill of an artisan of ordinary skill in the medical or tissue marking arts, and such an artisan will be able to understand what is a useful amount of microparticles for delivery to body tissue sites.

According to the invention, the microparticles can be contained and used for delivery in a tissue marking composition comprising an injectable combination of microparticles in a biocompatible carrier. The carrier can be any biocompatible fluid capable of delivering the microparticles to a desired tissue site. A carrier may include, for example, a biologically compatible suspension, solution, or other form of a fluid or gel. Examples of materials useful in biologically compatible carriers include saline, dextrans, glycerol, polyethylene glycol, corn oil or safflower oil, other polysaccharides or biocompatible polymers, methyl cellulose, glucan, agarose, etc., either singly or in combination.

The carrier can preferably be an aqueous suspension or solution, other fluid, or gel of polymeric chains of B–D glucose, commonly referred to as β-glucan. The glucose units are linked to each other at the 1–3, 1–4, or 1–6 positions and form polymeric chains ranging to several thousand daltons in weight.

β-glucan is a naturally occurring constituent of cell walls in essentially all living systems including plants, yeast, bacteria, and mammalian systems. Its effects and modulating actions on living systems have been studied extensively (see Abel, G., and Czop, J. K., "Stimulation of Human Monocyte B-glucan Receptors by Glucan Particles Induces Production of TNF-∂ and IL-B," Int. J. Immunopharmacol., 14(8) :1363–1373, 1992 and references included therein). β-glucan, when administered in experimental studies, elicits and augments host defense mechanisms including the steps required to promote healing by first intent, thereby stimulating the reparative processes in the host system. β-glucan is removed from tissue sites through macrophagic phagocytosis or by enzymatic destruction by serous enzymes. The destruction or removal of β-glucan, as well as its available viscosity and lubricous nature, make it a useful carrier for the microparticles in tissue marking applications.

Aqueous solutions, suspension, fluids, or gels of β-glucan can be produced that have favorable physical characteristics as a carrier for microparticles in tissue marking applications. The viscosity can vary from a thin liquid to a firm, self-supporting gel. Irrespective of viscosity, the β-glucan has excellent lubricity, thereby creating a particle-carrier composition which is easily administered by delivery to a predetermined body site through a small bore needle. A preferred β-glucan composition is β-D-glucan containing 4-0-linked-β-D-glycopyranosyl units and 3-0-linked-β-D-glycopyranosyl units. The carrier can be of sufficient viscosity to assure that the microparticles remain suspended therein, for a sufficient time duration to accomplish the injection procedure.

Another example of a preferred carrier material is methyl cellulose or another linear unbranched polysaccharide. Further examples of appropriate carrier materials include agarose, hyaluronic acid, polyvinyl pyrrolidone or a hydrogel derivative thereof, dextran or a hydrogel derivative thereof, glycerol, polyethylene glycol, succinylated collagen, liquid collagen, oil-based emulsions such as corn or safflower, or other polysaccharides or biocompatible organic polymers either singly or in combination with one or more of the above-referenced solutions.

The amount of microparticles to carrier in a tissue marking composition can be any amount that will provide a tissue marking composition that is flowable and injectable, and that will allow a desired amount of microparticles to be delivered to a tissue site. Preferred amounts of microparticles in a tissue marking composition can be in the range from about 20 to 60 percent by volume, more preferably from about 25 to 40 percent by volume.

In use, the tissue marking composition can typically be injected in a fluid state, e.g., as a slurry, suspension, or emulsion, through a needle, into a body tissue site. When deposited into a body tissue, the carrier will be carried away into the body, e.g., through the blood stream, and disperse or be destroyed. It is necessary that at least some of the microparticles, preferably most or substantially all of the microparticles, are substantially immobile upon delivery to a tissue site for marking. Microparticles used for tissue marking according to the invention are sufficiently immobile to be used for tissue marking applications; if the microparticles tend to move at all after delivery to a tissue site, the microparticles generally will do so only up the path of the needle used to inject them.

While subsequent portions of the description include language relating specifically to tissue marking in breast biopsy applications, all types of tissue marking applications are considered to be within the contemplation of the present invention. Examples include other types of biopsy applications such as colon, rectum, or prostate biopsies, and non-biopsy applications including tissue marking for other types of medical procedures such as tissue removal, e.g., the removal of polyps from the rectum or colon. Or, the tissue may be marked to provide a target for radiation treatment, i.e., detectable microparticles can be delivered to a tissue site to act as a target at which a beam of radiation can be precisely directed. One of ordinary skill in the medical or biopsy arts will understand and appreciate how detectable microparticles can be used in these and other tissue marking or biopsy processes e.g., by guiding a delivery apparatus to a desired body tissue and delivering an amount of the microparticles to the site, for detection at that site at a later time.

Factors that might be considered, controlled, or adjusted for in applying the process to a particular tissue marking application might include consideration of the composition of the microparticles; the amount of microparticles to be delivered to the body site; factors relating to the method of delivery including the particular equipment (e.g., needle or biopsy probe) used for delivery, and the method and route used to place the dispensing end of the delivery device at the desired body site; etc. All of these factors will be appreciated by one of ordinary skill in the tissue marking or medical arts, and can be readily dealt with to apply the described methods to a wide variety of tissue marking procedures.

Biopsy is a method by which a tissue sample is removed from a site of a body to diagnose the tissue as healthy or diseased, e.g., carcinogenic. Biopsies are performed on tissues of many different body organs, including prostate and breast tissues. The means used to perform the biopsy can include any equipment and techniques generally known or useful in biopsy procedures.

Breast biopsies can be performed using stereotactic, vacuum-assisted breast biopsy techniques and equipment therefore. Such techniques and equipment involve the use of minimally invasive instruments and techniques such as automated surgical biopsy devices. These methods and devices relate to percutaneous procedures that include inserting a needle-like instrument through a very small incision in the breast to access the tissue mass of interest and obtain a tissue sample for later examination and analysis. See, e.g., U.S. Pat. No. 6,086,544, incorporated herein by reference. It is not uncommon in modern breast biopsies, e.g., using a mammotone breast biopsy system sold under the trade name BIOPSYS, from Ethicon Endo-Surgery, Inc., for all evidence of a lesion to be removed during the biopsy.

According to the invention, detectable microparticles can be used to mark the site of a biopsy, e.g., a breast biopsy. The microparticles can be used to locate the biopsy site in case malignancy is determined, thereby enabling a return to the site and subsequent surgical treatment, e.g., excision, even if the mammographic findings associated with the original lesions were removed completely.

The detectable microparticles can be delivered to the site of the breast biopsy using any sort of a needle delivery system. According to a preferred method of the invention, microparticles can be delivered using the same biopsy equipment, e.g., the same biopsy sheath, as used to perform the biopsy, so as to achieve very precise marking of the biopsied site.

A rabbit research study was conducted to evaluate potential applications of radiopaque pyrolytic carbon coated zirconium oxide beads.

The following is a summary of the study results:

STUDY OBJECTIVE

The objective of the research study was to determine the qualitative and quantitive persistence of the radiopaque pyrolytic carbon coated beads.

MODEL DESCRIPTION

Rabbits were selected as the most appropriate species for this study for the following reasons: Auricular injection has frequently been used to quantify the persistence of materials. The cartilage in the ear provides a substrate over which the material can be inserted and subsequently measured. Migration from the insertion site proximally can be readily observed. Rabbits also provide a "non-growing" model. Therefore the effects of growth are not a study factor. The relative constancy of the landmarks in a smaller animal allows bony landmarks for dissection at necropsy.

The study called for injection of the carbon coated beads into rabbits in the following locations:

Ear subcutaneous tissue

Stomach/esophagus sub-mucosa

Large intestine/colon sub-mucosa

The rabbit's large intestine lining was found to be too thin for the injection needle and so the efforts in this location were abandoned; only the ear and stomach/esophagus locations were possible.

A total of 5 rabbits had injections (0.5–1.0 ml) in both ears and 2 rabbits had a total of 7 injections (0.25 ml each) in the intestine/stomach location.

Measurements

Persistence in location was measured by radiography and necropsy. Flat film radiographs were taken pre-and post-procedure to document persistence and non-migration. Radiographs were taken at sacrifice to document non-migration (stomach/esophagus).

Results

Ear

Procedure

Volumes between 0.5–10 ml of beads were injected in both ears of 5 rabbits. The beads were injected subcutaneously between the skin and the auricular cartilage on the convex surface of the ear using disposable 16-gauge needles. All ears were examined after injection and a x-ray of the ear was taken for record purposes.

1 Week Post-procedure

There were no evidence of swelling, inflammation or edema associated with the injection site or the injections.

2 Weeks Post-procedure

Minor reddish and swelling around each injected bulk was observed.

3 Weeks Post-procedure

All injection sites were easily visible with little evidence of redness or swelling.

5 Weeks Post-procedure

At 5 weeks post-procedure, rabbits #1 and #2 were necropsied.

The ears as well as the internal organs were examined grossly. Upon dissection of the periauricular tissue on the skull and anterior and posterior to the base of the ear, no beads were observed in the tissues.

The ears were examined for migration of beads from the site of injection. The examinations were accomplished by tran-illuminating the tissues with bright light. No particles were observed beyond the boundaries of the lesions.

Stomach/Esophagus

Procedure

Using the gastric model, multiple sub-serosal injections were made along the greater curvature of the stomach. Approximately 0.25 ml of material was injected at each of 4 sites in one rabbit and 3 sites in another rabbit. The injections were made using a 1-ml syringe of material and a 16-gauge needle.

2 Weeks Post-procedure

Observations were consistent with that of the ear data.

8 Week Post-Procedure

At 8 weeks post-procedure, following radiography, both rabbits were necropsied. The following summarizes the results:

There was no apparent loss of beads or migration of beads from the injection site.

No gross migration of particles on the surface of the stomach or on the surface of the abdominal structures was noted.

The injection sites appeared well healed with no evidence of erythema or swelling noted in or about the injection sites.

Gross examination of the abdominal structures did not demonstrate any gross abnormalities.

Summary of Study

Radiopaque carbon coated beads were injected subcutaneously between the skin and the auricular cartilage on the convex surface of ears, and subs-serosally along the greater curvature of the stomach in rabbits. Weekly examination demonstrated minimal inflammatory response to the injected area. At 5 weeks (ear) and 8 weeks (stomach/esophagus) post-procedure the radiopaque beads appeared stable in place.

What is claimed is:

1. A method for tissue marking the site of a prostate biopsy comprising delivering permanent to the site and detecting the microparticles.

2. A method for tissue marking the site of a polyp removal from a rectum or a colon comprising delivering detectable microparticles permanently wherein the particles can be permanently, detected at the site of the polyp removal.

* * * * *

UNITED STATES PATENT AND TRADEMARK OFFICE
CERTIFICATE OF CORRECTION

PATENT NO. : 6,394,965 B1  Page 1 of 1
DATED : May 28, 2002
INVENTOR(S) : Dean A. Klein It is certified that error appears in the above-identified patent and that said Letters Patent is hereby corrected as shown below:

Column 12,
Line 39 - 40, should read as follows:
1. A method for tissue marking the site of a prostrate biopsy comprising delivering detectable microparticles permanently to the site and detecting the microparticles.

Line 42 - 44, should read as follows:
2. A method for tissue marking the site of a polyp removal from a rectum or a colon comprising delivering detectable microparticles permanently, wherein the particles can be permanently detected at the site of the polyp removal.

Signed and Sealed this

Eighteenth Day of February, 2003

JAMES E. ROGAN
*Director of the United States Patent and Trademark Office*